United States Patent
Isaji et al.

(10) Patent No.: US 6,407,139 B1
(45) Date of Patent: Jun. 18, 2002

(54) NEOVASCULARIZATION INHIBITOR

(75) Inventors: Masayuki Isaji; Hiroshi Miyata; Yukiyoshi Ajisawa, all of Nagano (JP)

(73) Assignee: Kissei Pharmaceutical Co., Ltd. (JP)

( * ) Notice: Subject to any disclaimer, the term of this patent is extended or adjusted under 35 U.S.C. 154(b) by 0 days.

(21) Appl. No.: 09/125,036

(22) PCT Filed: Feb. 12, 1997

(86) PCT No.: PCT/JP97/00354

§ 371 (c)(1),
(2), (4) Date: Nov. 23, 1998

(87) PCT Pub. No.: WO97/29744

PCT Pub. Date: Aug. 21, 1997

(30) Foreign Application Priority Data

Feb. 15, 1996 (JP) ............................................... 8-65094

(51) Int. Cl.⁷ ............................................. A61K 31/195
(52) U.S. Cl. ....................................... 514/563; 514/912
(58) Field of Search .................................. 514/563, 912

(56) References Cited

U.S. PATENT DOCUMENTS

| | | |
|---|---|---|
| 5,385,935 A | 1/1995 | Tamai et al. |
| 5,512,591 A | 4/1996 | Halperin et al. |
| 5,733,327 A | 3/1998 | Igaki et al. |

FOREIGN PATENT DOCUMENTS

JP    5163222    6/1993

OTHER PUBLICATIONS

Chemical Abstracts 124:105948 (1995), Hishikawa et al.*
Abstract of "Inhibitory Effect Of Tranilast On Femoral Artery Intimal Thickening Spontaneously Hypertensive Rats" by Kikuchi, et. al., Japanese Journal f Pharmacology, 1994, vol. 64, No. Suppl. 1, pp. 165P.
Abstract of "Prominent Inhibitory Effects of Tranilast On Migration And Proliferation of Vascular Smooth Muscle Cells" by Tanaka, et. al., Cardiovascular Drugs and Therapy, 1993, vol. 7, No. Suppl. 2, pp. 451.
"Tranilast Suppresses Intimal Hyperplasia After Photochemically Induced Endothelial Injury In The Rat" by Kikuchi, et. al., Eur. J. Pharmacol., 1996, 295 (2/3), 221–7.
"Prominent Inhibitory Effects Of Tranilast On Migration And Proliferation Of And Collagen Synthesis By Vascular Smooth Muscle Cells" by Tanaka, et. al., Atherosclerosis (Shannon, Irel.), 1994, 107 (2), 179–85.
"Suppressive Effect Of An Antiallergic Drug, Tranilast, On The Vascular Intimal Thickening Induced By Balloon Catheter" by Ichikawa, et. al., Oyo Yakuri, 1995, 50 (5), 539–48.
"The Mechanism Involved In The Inhibitory Action of Tranilast On Collagen Biosynthesis of Keloid Fibroblasts" by Suzawa, et. al., Japan J. Pharmacol., 1992, vol. 60, pp. 91–96.

Japanese Journal of Cancer and Chemotherapy, vol. 20, No. 1, 1993 and English translation.
"Prominent Inhibitory Effects of Tranilast on Migration and Proliferation of and Collagen Synthesis by Vascular Smooth Muscle Cells", Tanaka, et. al., Atherosclerosis, 107 (1994) 179–185.
"Inhibition of PDGF– and TGF–β1–Induced Collagen Synthesis, Migration and Proliferation by Tranilast in Vascular Smooth Muscle Cells from Spontaneously Hypertensive Rats", Atherosclerosis, 118 (1995) 213–221.
Canadian Journal of Physiology and Pharmacology, vol. 74, No. 1, Jan. 1996.
"Inhibition of Angiogenesis Through Modulation of Collagen Metabolism", Ingber, et. al., The U.S. and Canadian Academy of Pathology, Inc., vol. 59, No. 1, pp. 44, 1988.
"Definition of Two Angiogenic Pathways by Distinct $\alpha_v$ Intergrins", Friedlander, et. al., Science, vol. 270, Dec. 1995.
"Involvement of Integrins $\alpha_v\beta_3$ and $\alpha_v\beta_5$ in Occular Neovascular Disease", Friedlander, Proc. Natl. Acad. Sci., vol. 93, pp. 9764–9769, Sep. 1996.
"Tranilast Suppresses Intimal Hyperplasia After Photochemically Induced Endothelial Injury in the Rat", European Journal of Pharmacology, 295 (1996) 221–227.
"Inhibition of Basement Membrane Biosynthesis Prevents Angiogenesis" Maragoudakis, et. al., The Journal of Pharmacology and Experimental Therapeutics, vol. 244, No. 2, 1987.
"Isolation and Characterization of an Inhibitor of Neovascularization from Scapular Chondrocytes", The Journal of Cell Biology, vol. 119, No. 2, Oct. 1992, 475–482.
"A Possible Mechanism for Inhibition of Angiogenesis by Angiostatic Steroids: Induction of Capillary Basement Membrane Dissolution", Ingber, et. al., Endocrinology, vol. 119, No. 4, p. 68–75, Oct. 1986.
International Search Report, PCT/JP97/00354, May 27, 1997.

* cited by examiner

Primary Examiner—Zohreh Fay
(74) Attorney, Agent, or Firm—Stuart D. Frenkel

(57) ABSTRACT

The present invention relates to a neovascularization inhibitor comprising as the active ingredient N-(3,4-dimethoxycinnamoyl) anthranilic acid represented by the formula:

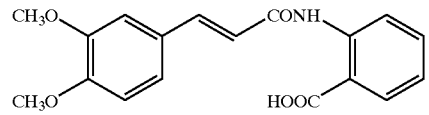

or a pharmaceutically acceptable salt thereof, which has inhibitory effects on proliferation and chemotaxis of human microvascular endothelial cells and tube formation of human microvascular endothelial cells, and therefore, is useful as an agent for the prevention and treatment of diseases associated with neovascularization such as diabetic retino senile discoid macular degeneration, neovascular glaucoma and rheumatic arthritis.

11 Claims, 2 Drawing Sheets

NEOVASCULARIZATION INHIBITOR

This application is a 371 of Pct/JP97/00354 filed on Feb. 12, 1997.

FIELD OF THE INVENTION

The present invention relates to a pharmaceutical composition which is useful as a neovascularization inhibitor.

More particularly, the present invention relates to an agent for the prevention or treatment of diseases associated with neovascularization which comprises as the active ingredient N-(3,4-dimethoxycinnamoyl)anthranilic acid represented by the formula:

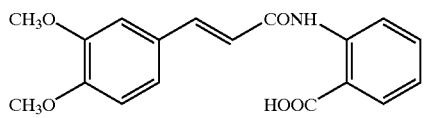

(I)

or a pharmaceutically acceptable salt thereof.

Diseases associated with neovascularization which can be treated in accordance with this invention include, various diseases which occur by participation of neovascularization as one of the causes thereof for examples include, diabetic retinopathy, senile discoid macular degeneration, retinopathy of prematurity, sickle-cell retinopathy, retinal vein occlusion, neovascularization after corneal transplantation or cataract extraction, neovascular glaucoma, rubeosis iridis, rheumatic arthritis, psoriasis, scleredema, tumors, overgrowth of capillary blood vessels in atherosclerosis adventitia and corneal neovascularization caused by long wear of cantact lens.

BACKGROUND OF THE INVENTION

In general, neovascularization is a phenomena accompanying degradation of the basement membrane by proteolytic enzymes, chemotaxis and proliferation of endothelial cells, tube formation by endothelial cell differentiation and reorganization of blood vessels. Neovascularization occurs in luteinization and placentation physiologically and in the diseases described above pathologically. For example, in retinopathy, retinal tissues lying between preexisting basement membrane around retinal vessels and vitreous are degraded. Subsequently endothelial cells of preexisting vessels migrate from junctions of the degraded retinal tissues and endothelial cells proliferate to fill up spaces left by the migrated endothelial cells migrated, and the endothelial cells migrated to vitreoretina reorganize new vessels, leading to neovascularization.

Neovascularization is correlated with various diseases, and, for example, neovascularization plays a close part in the process of the onset and progress of the above diseases. Therefore, extensive studies to find compounds having an inhibitory activity on neovascularization have been actively promoted for the prevention or treatment of these diseases. Although, for example, neovascularization inhibitors such as fumagillin analogues, which are microbial metabolites having an inhibitory activity on endothelial cell proliferation, tetracycline antibiotics, which can inhibit a collagenase activity, and microorganism-derived D-glucogalactan sulfate, which can interfere with binding of heparin-binding angiogenic factors to their receptors, are known, there is no satisfying drug clinically. In addition, there is no procedure enough to treat the above diseases. Specially, if patients with diabetic retinopathy do not undergo surgical treatment, involution of neogenetic vessels can not be observed, and therefore, visual loss caused by a discharge of blood from neogenetic vessels has become a problem. Thus, development of drugs having an excellent effect on neovascularization has been greatly desired.

N-(3,4-Dimethoxycinnamoyl)anthranilic acid (generic name: Tranilast) represented by the above formula (I) of the present invention has been used widely as a drug for the treatment of allergic disorders such as bronchial asthma, allergic rhinitis, atopic dermatitis and allergic conjunctivitis, and cutaneous disorders such as keloid and hypertrophic scar. For example, it has been known that Tranilast has inhibitory activities on chemical mediator release caused by an allergic reaction, excessive collagen accumulation by fibroblast cells in cutaneous tissues and excessive proliferation of smooth muscle cells in coronary artery vessels.

However, it is disclosed in no way that Tranilast suppresses proliferation and chemotaxis of microvascular endothelial cells and tube formation of microvascular endothelial cells, and it is not known at all that Tranilast is useful as a neovascularization inhibitor.

DISCLOSURE OF INVENTION

The present invention relates to a neovascularization inhibitor which comprises as the active ingredient N-(3,4-dimethoxycinnamoyl)anthranilic acid represented by the formula:

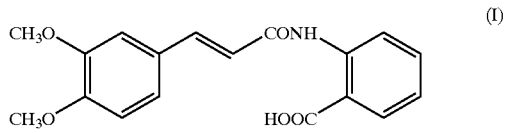

(I)

or a pharmaceutically acceptable salt thereof.

The present invention relates to a method for the prevention and treatment of diseases associated with neovascularization which comprises administering N-(3,4-dimethoxycinnamoyl)anthranilic acid represented by the above formula (I) or a pharmaceutically acceptable salt thereof.

The present invention relates to a use of N-(3,4-dimethoxycinnamoyl)anthranilic acid represented by the above formula (I) or a pharmaceutically acceptable salt thereof for the manufacture of a pharmaceutical composition for the prevention and treatment of diseases associated with neovascularization.

Furthermore, the present invention relates to a use of N-(3,4-dimethoxycinnamoyl)anthranilic acid represented by the above formula (I) or a pharmaceutically acceptable salt thereof as a neovascularization inhibitor.

BEST MODE FOR CARRYING OUT THE INVENTION

Figure 1:
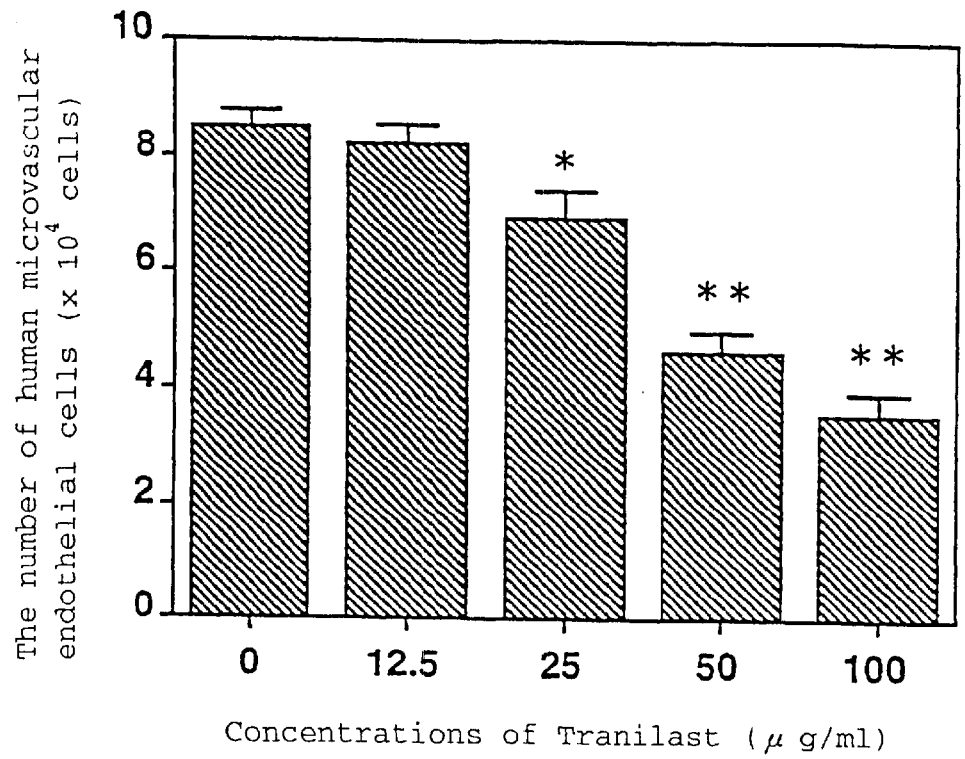
FIG. 1 is a graph illustrating the inhibitory effect of Tranilast on proliferation of human microvascular endothelial cells. The axis of the ordinates shows the number of human microvascular endothelial cells ($\times 10^4$ cells), and the axis of the abscissas shows concentrations of Tranilast ($\mu$g/ml). The symbols * and ** in the graph show the significantly difference at $p<0.05$ and $p<0.01$, respectively.

The present inventors have been extensively studied to find compounds having an inhibitory activity on neovascularization. As a result, it was found that N-(3,4-dimethoxycinnamoyl) anthranilic acid (generic name: Tranilast) represented by the above formula (I) has remarked inhibitory effects on proliferation of human microvascular endothelial cells, chemotaxis of human microvascular endothelial cells and tube formation of human microvascular endothelial cells, and therefore, is extremely useful as a neovascularization inhibitor, thereby forming the basis of the present invention.

Accordingly, the present inventors confirmed that Tranilast significantly suppressed proliferation of human microvascular endothelial cells in the in vitro cell proliferation inhibitory activity test using human microvascular endothelial cells.

The present inventors also confirmed that Tranilast significantly suppressed chemotaxis of human microvascular endothelial cells in the in vitro cell chemotaxis inhibitory activity test using human microvascular endothelial cells.

Furthermore, the present inventors also confirmed that Tranilast significantly inhibited tube formation of human microvascular endothelial cells in the in vitro cell tube formation inhibitory activity test using human microvascular endothelial cells.

As a consequence, Tranilast has excellent inhibitory effects on proliferation and chemotaxis in human microvascular endothelial cells, and therefore, is a compound being useful as a neovascularization inhibitor. Furthermore, Tranilast has an excellent inhibitory effect on tube formation of human microvascular endothelial cells, and therefore, is a compound being extremely useful as an agent for the prevention and treatment of diseases associated with neovascularization.

Therefore, pharmaceutical compositions which are useful as agents for the prevention and treatment of diseases associated with neovascularization can be prepared by comprising as the active ingredient Tranilast or a pharmaceutically acceptable salt thereof.

Various methods for the preparation of Tranilast and pharmaceutically acceptable salts thereof are known (Japanese Patent Application Publication (kokoku) No.Sho.56-40710; ibid. No.Sho.57-36905; ibid. No.Sho.58-17186; ibid. No.Sho.58-48545; ibid. No.Sho.58-55138; ibid. No.Sho.58-55139; ibid. No.Hei. 01-28013; ibid. No.Hei.01-50219; ibid. No.Hei.03-37539 etc.). For example, Tranilast and pharmaceutically acceptable salts thereof can be prepared by allowing a reactive functional derivative such as acid halide and acid anhydride of 3,4-dimethoxycinnamoyl acid represented by the formula:

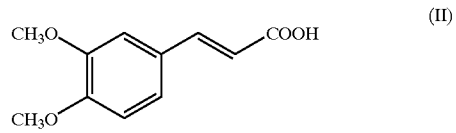
(II)

to react with anthranilic acid represented by the formula:

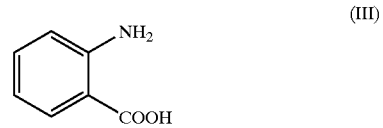
(III)

in the usual way, and if desired, converting the resulting compound into a salt thereof.

As examples of pharmaceutically acceptable salts of Tranilast, salts with inorganic bases such as a sodium salt and a potassium salt, salts formed with organic amines such as morpholine, piperazine and pyrrolidine and salts formed with amino acids can be illustrated.

When the pharmaceutical compositions of the present invention are employed in the practical treatment, various dosage forms of pharmaceutical compositions can be used depending upon usage. As examples of such dosage forms, powders, granules, fine granules, dry sirups, tablets, capsules, ointments, injections, eye drops and the like can be illustrated.

These pharmaceutical compositions can be formulated by admixing, diluting or dissolving occasionally with appropriate pharmaceutical additives such as excipients, disintegrators, binders, lubricants, diluents, buffers, isotonicities, antiseptics, moistening agents, emulsifiers, dispersing agents, stabilizing agents and dissolving aids in accordance with conventional methods and formulating in the usual way depending upon the dosage forms.

For example, powders can be formulated by admixing well Tranilast represented by the formula (I) or a pharmaceutically acceptable salt with appropriate excipients, lubricants and the like occasionally.

Tablets can be formulated by admixing Tranilast or a pharmaceutically acceptable salt with appropriate excipients, disintegrators, binders, lubricants and the like occasionally, and pressing the mixture in the usual way. The tablets also can be coated to provide film-coated tablets, sugar-coated tablets, enteric coating tablets and the like.

For example, capsules can be formulated by admixing well appropriate excipients, lubricants and the like occasionally, and filling the mixture in capsules. Capsules can be also formulated by forming granules or fine granules in the usual way, and filling the granules or fine granules in capsules.

Ointments can be used as eye ointments.

Injections can be injected directly into diseased tissues such as cornea and vitreous or their adjacent tissues by using a fine needle, and can be also used as intraocular perfusate.

The pharmaceutical compositions of the present invention can be administered as sustained release preparations. For example, Tranilast preparation is incorporated into pellet or microcapsule of sustained release polymer as a sustained release preparation, and the pellet or microcapsule is surgically planted into tissues to be treated. As examples of sustained release polymers, ethylene-vinylacatate copolymer, polyhydro-metacrylate, polyacrylamide, polyvinylpirrolidone, methylcellulose, lactic acid polymer, lactic acid-glycolic acid copolymer and the like can be illustrated, and preferably, biodegradable polymer such as lactic acid polymer and lactic acid-glycolic acid copolymer can be illustrated.

When the pharmaceutical compositions of the present invention are employed in the practical treatment, the dosage of Tranilast or a pharmaceutically acceptable salt thereof as the active ingredient is appropriately decided depending on the body weight, age, sex, degree of symptoms and the like of each patient to be treated, which is approximately within the range of from 100 to 1,000 mg per day per adult human in the case of oral administration and approximately within the range of from 20 $\mu$g to 300 mg per day per adult human in the case of parenteral administration.

The dose of Tranilast or a pharmaceutically acceptable salt thereof can be appropriately increase and decrease depending on the type of diseases, degree of symptoms of each patient to be treated and therapeutic value.

EXAMPLES

The present invention is further illustrated in more detail by way of the following Examples.

Study to Confirm Inhibitory Effect on Neovascularization

Example 1

Inhibition of Proliferation of Human Microvascular Endothelial Cells

① Culture of Human Microvascular Endothelial Cells

Normal human dermal microvascular endothelial cells (Cell Systems Corporation) were subcultured in a medium (MVE medium, Cell Systems Corporation) for endothelial cell culture and used for the study. At the logarithmic growth phase, the medium was aspirated and cells were washed with phosphate-buffered saline (PBS(–)) which was added gently. Then, the PBS(–) was aspirated, an aliquot of 0.25% trypsin solution containing 0.02% EDTA was added to the culture plate, and the morphology of cells was observed under a phase-contrast microscopy. When cells were going to be round, an equal value of MVE medium was added to the trypsin solution to stop the action of trypsin. Attached cells were harvested from the plate by pipetting the medium using a slender pasture pipette. Cell suspension was transferred into spit, then medium was added to the spit, and the cell suspension was mixed about 20 times vigorously by pipetting with a pasture pipete and centrifuged at 100–110×g for 1 minute. After the supernatant was discarded, fresh medium was added to the precipitate, and cell suspension was prepared by pipetting using a pasture pipete. Number of viable cells in an aliquot of the suspension was counted under a phase-contrast microscopy using a hemocytometer. Cell concentration was adjusted to 2×10$^4$ cells/ml.

② Preparation of Test Drug

Tranilast was added to 1% aqueous sodium bicarbonate solution to prepare 0.55% solution and dissolved by warming at 70° C. The solution was sterilized with millipore filter and diluted with MVE medium to a final prescribed concentration.

③ Experimental Method

Cell suspension (1 ml) was added to collagen-coated 6-well plate(Toyobo Engineering Co., Ltd.) and cultured at 37° C. under a humidified atmosphere of 5% $CO_2$ in air. After 1 day, the medium was aspirated, cells were washed with PBS(–), and 1 ml of fresh medium and 0.1 ml of various concentrations of Tranilast solution were added to the plate and the plate was incubated for further 2 days. After incubation, the medium was aspirated, cells were washed with PBS(–), and then 1 ml of 0.25% trypsin solution containing 0.02% EDTA was added to the plate. After harvesting cells from the plate by pipetting using a pasture pipete, number of viable cells was counted using a hemocytometer.

④ Assessment of Effect

Mean and standard variation value of each group were calculated. Statistical analysis of significance was performed by a one-way analysis of variance and statistical significance was confirmed. Thereafter, analysis of significance between groups was performed by Dunnett's multiple test.

⑤ Results

As shown in FIG. 1, Tranilast significantly suppressed the proliferation of human microvascular endothelial cells in a concentration-dependent manner.

Example 2

Inhibition of Chemotaxis of Human Microvascular Endothelial Cells

① Culture of Human Microvascular Endothelial Cells

According to the method of Example 1 ①, human microvascular endothelial cells were cultured to prepare a cell suspension. Number of viable cells was counted under a phase-contrast microscopy using a hemocytometer and cell concentration was adjusted to 2×10$^4$ cells/ml.

② Preparation of Test Drug

Tranilast was added to 1% aqueous sodium bicarbonate solution to prepare 0.55% solution and dissolved by warming at 70° C. The solution was sterilized with millipore filter and diluted with DMEM+Ham (1:1) medium to a prescribed final concentration.

③ Experimental Method

Chemotaxis of human dermal microvascular endothelial cells (prepared in ①) to vascular endothelial growth factor (VEGF) was studied using a 96-well micro chemotaxis chamber (Neuro Probe Inc.). An aliquot (32 $\mu$l) of DMEM+ Ham (1:1) medium containing 100 ng/ml of VEGF, 0.1% bovine serum and various concentrations of Tranilast was added to the lower cavity of the chemotaxis chamber. An aliquot (50 $\mu$l) of medium containing cell suspension and Tranilast was added to the upper cavity of the chamber. Polycarbonate filter (10 $\mu$m thickness with 8 $\mu$m pore size; Neuro Probe Inc.) coated with type-1 collagen was used for the chemotaxis membrane. The chemotaxis chamber was incubated at 37° C. for 5 hours under a humidified atmosphere of 5% $CO_2$ in air. Cells migrated to the lower side of the filter were fixed with 90% ethanol, and stained with Diff-Quick (Baxter Diagnostics Inc.). Number of migrated cells was counted in 5 random fields at ×400 magnification under a phase-contrast microscopy and mean chemotaxis cell number was calculated.

④ Assessment of Effect

Mean and standard variation value of each group were calculated. Statistical analysis of significance was performed by a one-way analysis of variance and statistical significance was confirmed. Thereafter, analysis of significance between groups was performed by Dunnett's multiple test.

⑤ Results

Figure 2:
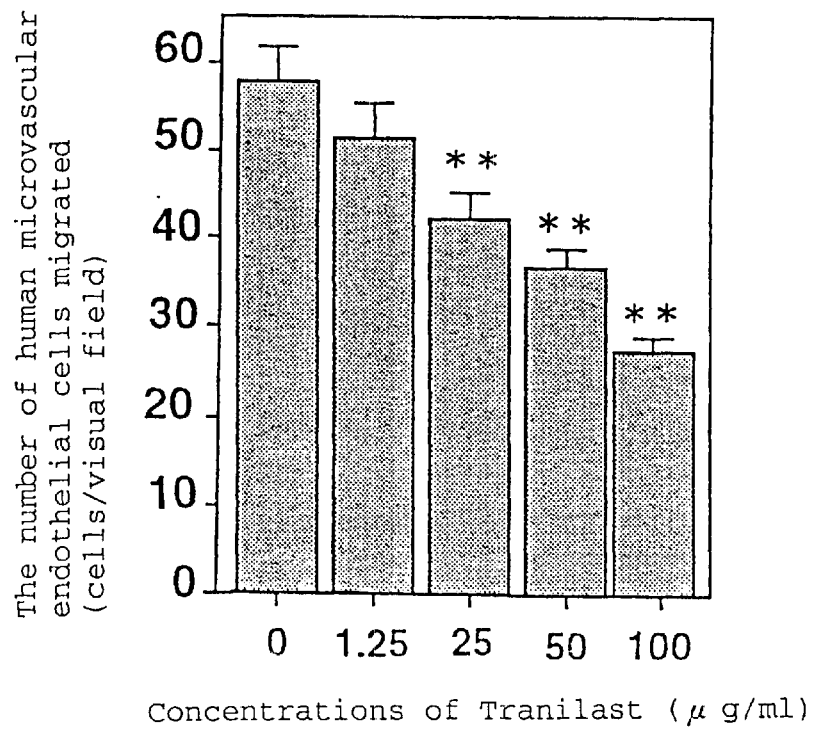
FIG. 2 is a graph illustrating the inhibitory effect of Tranilast on chemotaxis of human microvascular endothelial cells. The axis of the ordinates shows the number of human microvascular endothelial cells migrated (cells/visual field), and the axis of the abscissas shows concentrations of Tranilast (μg/ml). The symbol** in the graph shows the significantly difference at p<0.01.

As shown in FIG. 2, Tranilast significantly suppressed the chemotaxis of human microvascular endothelial cells in a concentration-dependent manner.

Example 3

Tube Formation of Human Microvascular Endothelial Cells

① Culture of Human Microvascular Endothelial Cells

According to the method of Example 1 ①, human microvascular endothelial cells were cultured to prepare a cell suspension. Number of viable cells was counted under a phase-contrast microscopy using a hemocytometer and cell concentration was adjusted to $4 \times 10^4$ cells/ml.

② Preparation of Test Drug

Tranilast was added to 1% aqueous sodium bicarbonate solution to prepare 0.5% solution and dissolved by warming at 70° C. The solution was sterilized with millipore filter and diluted with MVE medium to a prescribed final concentration.

③ Experimental Method

An aliquot (0.25 ml) of matrigel (10 mg/ml, Becton Dickinson Labware) was added to a 24-well culture plate (Corning) and was then allowed to solidify by incubation at 37° C. for 1 hour. Suspension (0.25 ml) of human microvascular endothelial cells ($4 \times 10^4$ cells) and MVE medium (0.25 ml) containing various concentrations of Tranilast were added onto the gel. After 18 hours incubation at 37° C., 5 random fields of one well were observed at ×100 magnification using a phase-contrast microscopy and the number of formed network was counted.

④ Result

Figure 3:
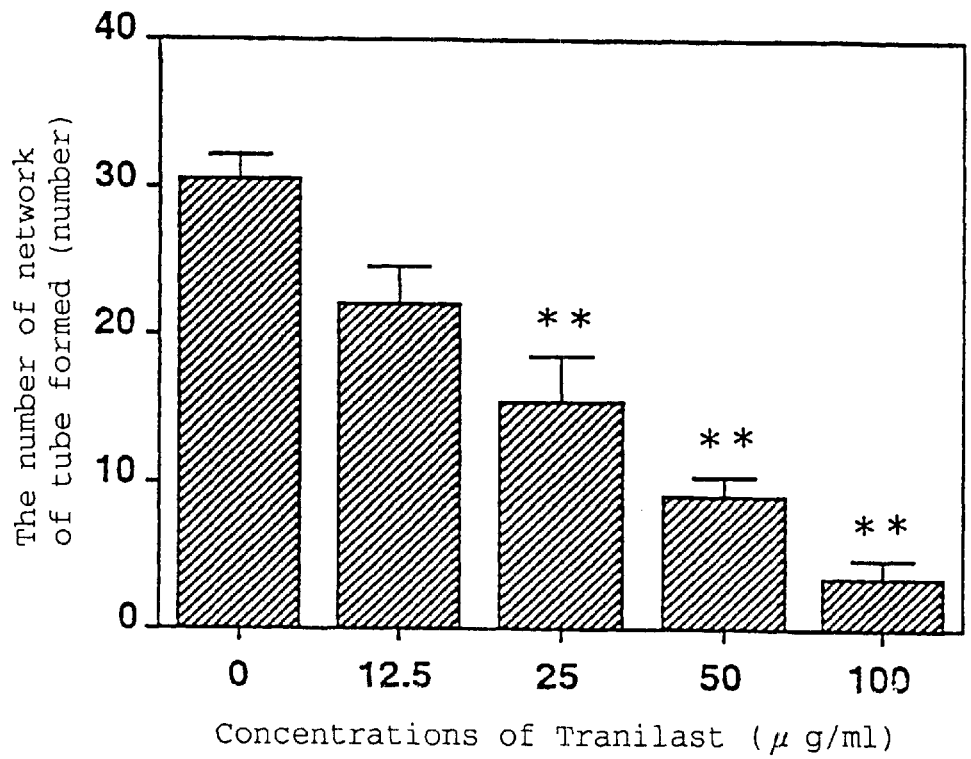
FIG. 3 is a graph illustrating the inhibitory effect of Tranilast on tube formation of human microvascular endothelial cells. The axis of the ordinates shows the number of network of tube formed (number), and the axis of the abscissas shows concentrations of Tranilast (μg/ml). The symbol**in the graph shows the significantly difference at p<0.01.

As shown in FIG. 3, number of the formed network was significantly reduced in a concentration-dependent manner.

Example 4

Tube Formation of Human Microvascular Endothelial Cells

① Culture of Human Microvascular Endothelial Cells

According to the method of Example 1 ①, human microvascular endothelial cells were cultured to prepare a cell suspension. Number of viable cells was counted under a phase-contrast microscopy using a hemocytometer and cell concentration was adjusted to $4 \times 10^4$ cells/ml.

② Preparation of Test Drug

Tranilast was added to 1% aqueous sodium bicarbonate solution to prepare 1.0% solution and dissolved by warming at 70° C. The solution was sterilized with millipore filter and diluted with MVE medium to a prescribed final concentration.

③ Experimental Method

An aliquot (0.25 ml) of matrigel (10 mg/ml, Becton Dickinson Labware) was added to a 24-well culture plate (Corning) and was then allowed to solidify by incubation at 37° C. for 1 hour. Suspension (0.25 ml) of human microvascular endothelial cells ($4 \times 10^4$ cells) and MVE medium (0.25 ml) containing various concentrations of Tranilast were added onto the gel. After 18 hours incubation at 37° C., 5 random fields of one well were photographed at ×40 magnification using a phase-contrast microscopy. The lengths of the tube structures were measured and the mean value was calculated.

④ Result

Figure 4:
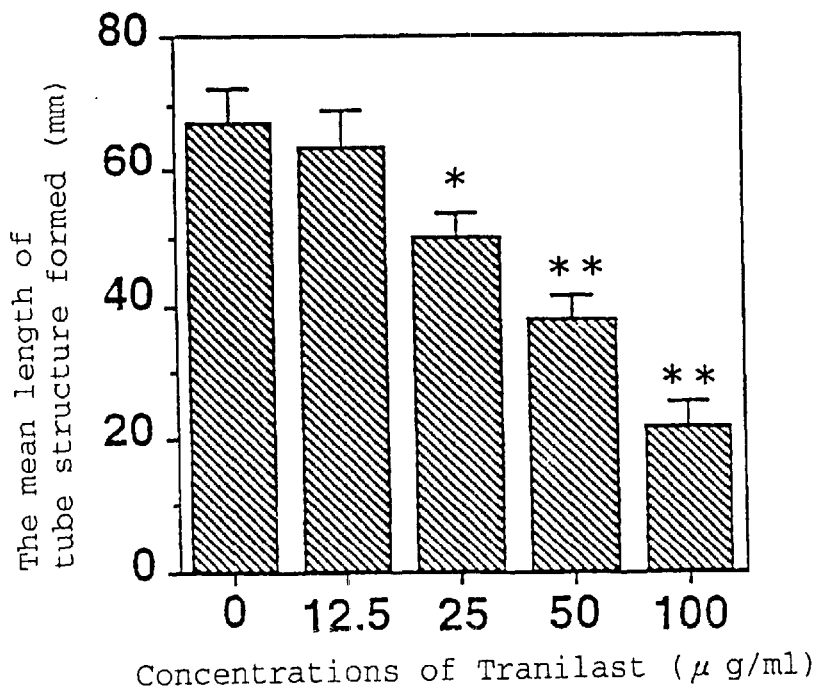
FIG. 4 is a graph illustrating the inhibitory effect of Tranilast on tube formation of human microvascular endothelial cells. The axis of the ordinates shows the mean length of tube structure formed (mm), and the axis of the abscissas shows concentrations of Tranilast (μg/ml). The symbols*and**in the graph show the significantly difference at p<0.05 and p<0.01, respectively.

As shown in FIG. 4, the length of the tube strucure was significantly reduced in a concentration-dependent manner.

Industrial Applicability

A pharmaceutical composition comprising as the active ingredient Tranilast has remarked inhibitory effects on proliferation and chemotaxis of human microvascular endothelial cells and tube formation of human microvascular endothelial cells, and therefore, is extremely effective as a neovascularization inhibitor.

What is claimed is:

1. A method for the prevention and treatment of diseases associated with neovascularization which comprises administering N-(3,4-dimethoxycinnamoyl)anthranilic acid represented by the formula:

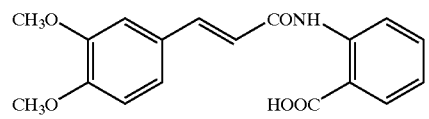

or pharmaceutically acceptable salt thereof to a human Patient showing symptoms of diseases associated with neovascularization.

2. The method as claimed in claim 1 wherein the disease to be treated is diabetic retinopathy.

3. The method as claimed in claim 1 wherein the disease to be treated is senile discoid macular degeneration.

4. The method as claimed in claim 1 wherein the disease to be treated is rheumatic arthritis.

5. The method as claimed in claim 1 wherein the disease to be treated is a tumor.

6. The method of claims 1, wherein said N-(3,4-dimethoxycinnamoyl) anthranilic acid is administered orally.

7. The method of claim 6, wherein said N-(3,4-dimethoxycinnamoyl) anthranilic acid is administered orally within the range of 100 to 1,000 mg per day.

8. The method of claim 1, wherein said N-(3,4-dimethoxycinnamoyl) anthranilic acid is administered parenterally.

9. The method of claim 8, wherein said N-(3,4-dimethoxycinnamoyl) anthranilic acid is administered parenterally in an amount of 20 μg to 300 mg per day.

10. The method of claim 1, wherein said N-(3,4-dimethoxycinnamoyl) anthranilic acid is administered as a topical, ointment.

11. The method of claim 1, wherein said N-(3,4-dimethoxycinnamoyl) anthranilic acid is administered as eye drops.

* * * * *